(12) United States Patent
Stiffler

(10) Patent No.: US 10,987,471 B2
(45) Date of Patent: Apr. 27, 2021

(54) INJECTION DEVICE DRIVE WITH TWO GEAR PATTERNS

(71) Applicant: Eli Lilly and Company, Indianapolis, IN (US)

(72) Inventor: Scott Matthew Stiffler, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 493 days.

(21) Appl. No.: 15/571,267

(22) PCT Filed: May 12, 2016

(86) PCT No.: PCT/US2016/032136
§ 371 (c)(1),
(2) Date: Nov. 2, 2017

(87) PCT Pub. No.: WO2016/186965
PCT Pub. Date: Nov. 24, 2016

(65) Prior Publication Data
US 2018/0339110 A1 Nov. 29, 2018

Related U.S. Application Data

(60) Provisional application No. 62/164,778, filed on May 21, 2015.

(51) Int. Cl.
*A61M 5/315* (2006.01)
*A61M 5/24* (2006.01)
*A61M 5/31* (2006.01)

(52) U.S. Cl.
CPC .......... *A61M 5/31558* (2013.01); *A61M 5/24* (2013.01); *A61M 5/2429* (2013.01);
(Continued)

(58) Field of Classification Search
CPC .......... A61M 5/31558; A61M 5/31575; A61M 5/31551; A61M 5/31528; A61M 5/31556;
(Continued)

(56) References Cited

U.S. PATENT DOCUMENTS

| 2006/0069355 A1* | 3/2006 | Judson | A61M 5/31511 |
| | | | 604/211 |
| 2007/0060894 A1* | 3/2007 | Dai | A61M 5/19 |
| | | | 604/207 |

(Continued)

FOREIGN PATENT DOCUMENTS

| GB | 1490040 | 10/1977 |
| JP | 2005520646 | 10/2003 |

(Continued)

OTHER PUBLICATIONS

Patent Cooperation Treaty International Search Report and Written Opinion of the International Searching Authority pertaining to International Application No. PCT/US2016/032136; International Filing Date: May 12, 2016; dated Nov. 15, 2016.

*Primary Examiner* — Bhisma Mehta
*Assistant Examiner* — James D Ponton
(74) *Attorney, Agent, or Firm* — M. Daniel Spillman

(57) ABSTRACT

An injection device having a drive member with first and second gear patterns that are fixed relative to each other. The drive member is rotatable and translatable in first and second opposing axial directions. A plunger expels medicament from a cartridge when it is translated in an advancing direction. A dosage indicator indicates a set dosage. A first gearing arrangement operably couples the first gear pattern with the plunger wherein rotation of the drive member in a first direction translates the drive member in a first axial direction without movement of the plunger and translation of the drive member in the opposite axial direction drives the plunger in the advancing direction. A second gearing (Continued)

arrangement operably couples the second gear pattern with the dosage indicator and moves the dosage indicator to indicate an increase in the set dosage when the drive member is translated in the first axial direction.

20 Claims, 4 Drawing Sheets

(52) U.S. Cl.
CPC .... A61M 5/31551 (2013.01); A61M 5/31575 (2013.01); A61M 5/31593 (2013.01); A61M 2005/2407 (2013.01); A61M 2005/2485 (2013.01); A61M 2005/3126 (2013.01); A61M 2005/3152 (2013.01)

(58) Field of Classification Search
CPC ...... A61M 5/31593; A61M 2005/3126; A61M 2005/3152; A61M 5/24; A61M 5/2429; A61M 2005/2407; A61M 2005/2485

See application file for complete search history.

(56) References Cited

U.S. PATENT DOCUMENTS

| 2007/0093761 A1* | 4/2007 | Veasey | A61M 5/31528 |
| | | | 604/207 |
| 2009/0275916 A1* | 11/2009 | Harms | A61M 5/31541 |
| | | | 604/506 |

FOREIGN PATENT DOCUMENTS

| WO | 2003080160 | 10/2003 |
| WO | 2004035113 | 4/2004 |
| WO | 2014166900 | 10/2014 |
| WO | 2015007816 | 1/2015 |

* cited by examiner

INJECTION DEVICE DRIVE WITH TWO GEAR PATTERNS

BACKGROUND

The present invention relates to injection devices and drive mechanisms employed with such injection devices.

Patients suffering from a number of different diseases are required to undergo numerous injections of an appropriate medicament for their ailment. Oftentimes, such patients set the dosage and perform the injection themselves. Various injection devices, such as injection pens for delivering insulin or other medicaments, have been developed which allow the patient to set the desired dosage and perform the injection themselves.

While a number of such injection devices are known in the art, further improvements remain desirable.

SUMMARY

The present invention provides an injection device that allows a patient to set a desired dosage and perform the injection themselves and which also has a relatively simple design thereby promoting efficient manufacture and robust performance.

The invention comprises, in one form thereof, an injection device for use with a medicament cartridge. The injection device includes a drive member defining an axis and having first and second gear patterns wherein the first and second gear patterns are fixed relative to each other. The drive member is rotatable about the axis and translatable in first and second opposing axial directions. A plunger having an elongate stem is couplable with the cartridge to expel medicament from the cartridge when the plunger is translated in an advancing direction. A dosage indicator is moveable to indicate a set dosage. A first gearing arrangement operably couples the first gear pattern with the plunger wherein rotation of drive member in a first rotational direction translates the drive member in the first axial direction without movement of the plunger and wherein translation of the drive member in the second axial direction drives the plunger in the advancing direction. A second gearing arrangement operably couples the second gear pattern with the dosage indicator wherein the second gearing arrangement moves the dosage indicator to indicate an increase in the set dosage when the drive member is translated in the first axial direction.

In some embodiments, the first and second gear patterns are axially displaced relative to each other. The first gear pattern may also advantageously define a worm gear. It may also be advantageous for the drive member to take the form of an elongate shaft with the second gear pattern being a plurality of annular gear teeth defining a pitch angle of 0 degrees.

Some embodiments have a first gearing arrangement that includes a first rotatable gear member engaged with the first gear pattern and a one-way clutch operably coupled with the first rotatable gear member wherein the one-way clutch prevents rotation of the first gear member when the drive member is rotated in the first rotational direction and wherein translation of the drive member in the second axial direction rotates the first gear member to thereby drive the plunger. Such a first gearing arrangement may also include a second rotatable gear member that is coupled with the first rotatable gear member and a rack coupled with the plunger wherein the second rotatable gear member is engageable with the rack.

In such embodiments having a first gearing arrangement with first and second rotatable gear members, the first and second rotatable gear members may advantageously define a non-unitary gear ratio. In such embodiments, it may also be advantageous for the first and second rotatable gear members to be fixed to a common shaft.

In some embodiments, movement of the second gearing arrangement generated by the drive member is exclusively due to the translation of the drive member and movement of the second gearing arrangement is independent of the rotational position and rotational movement of the drive member. In still other embodiments, the second gearing arrangement moves the dosage indicator to indicate a decrease in the set dosage when the drive member is translated in the second axial direction.

Some embodiments may have a second gearing arrangement that includes a third rotatable gear member engaged with the second gear pattern and operably coupled with the dosage indicator. In such embodiments, the dosage indicator may be fixed relative to the third rotatable gear member.

In still other embodiments, the injection device may include a housing at least partially enclosing the injection device and a manually operable actuator assembly operably coupled with the drive member. The actuator assembly is at least partially disposed external to the housing. The actuator assembly includes an actuating member that is rotatable to set a selected dose and axially translatable to inject the selected dose. In some embodiments including an actuator assembly, the actuator assembly also includes a keyway and a biasing member. The keyway is disposed proximate the drive member and is rotationally fixed relative to the drive member axis. The actuating member is axially moveable relative to the keyway between a dose setting position and an injection position and is rotationally and axially coupled with the drive member. In the dose setting position the actuating member is rotatable about the drive member axis and rotation of the actuating member rotates the drive member. In the injection position, the actuating member is engaged with the keyway thereby rotationally fixing the actuating member relative to the drive member axis and wherein axial movement of the actuating member in the second axial direction drives the drive member in the second axial direction. The biasing member is operably coupled with the actuating member and biases the actuating member toward the dose setting position.

In some embodiments having an actuator assembly, the actuator assembly many include a sleeve member wherein the sleeve member is rotationally fixed relative to the drive member axis and has the keyway disposed thereon. In such an embodiment, it may be advantageous for the sleeve member and the actuating member to be axially aligned with the drive member, wherein the sleeve member is non-rotationally slidable relative to the housing in the first and second axial directions and the biasing member is operably disposed between the sleeve member and the actuating member.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings wherein.

Figure 1:
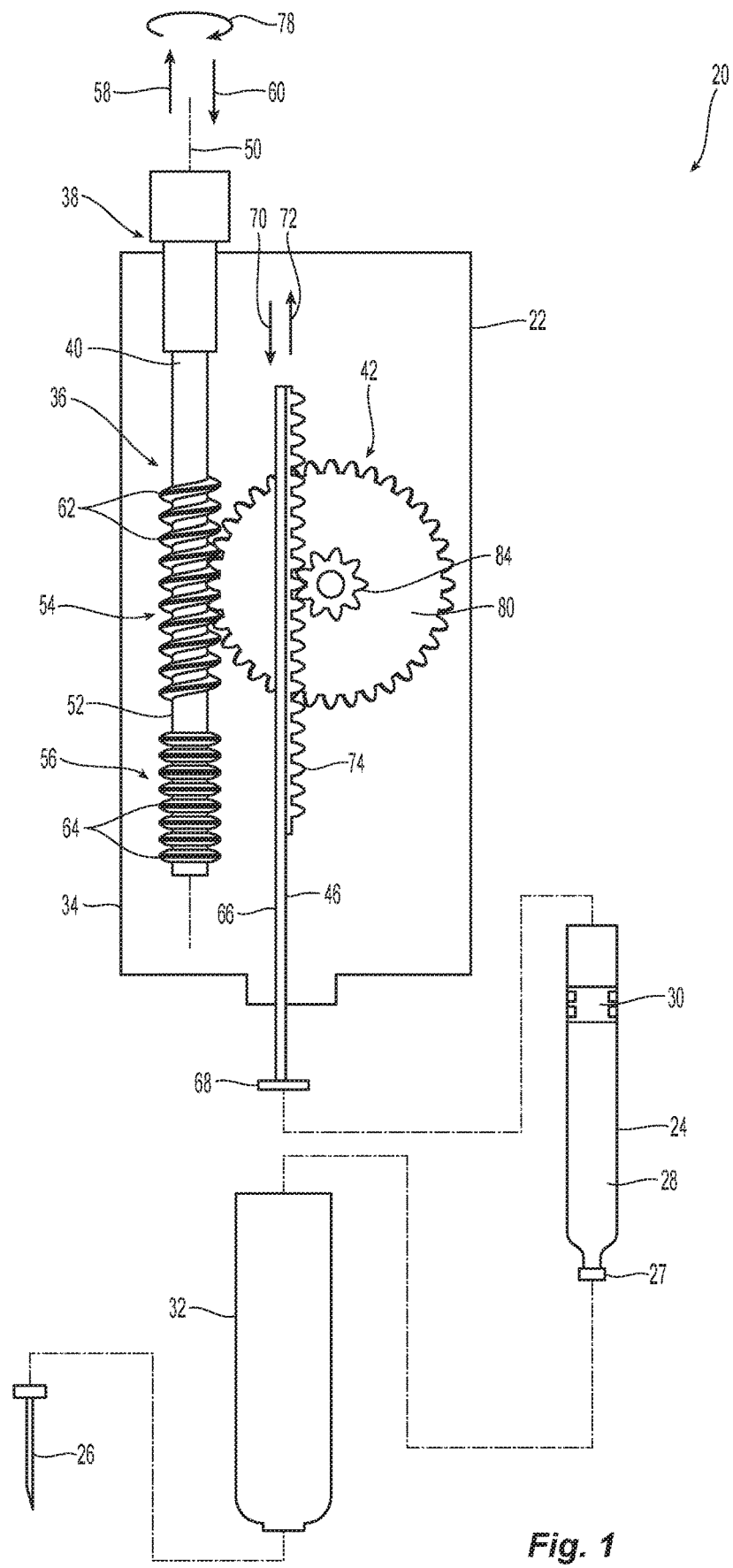
FIG. 1 is a schematic representation of an injection device.

Corresponding reference characters indicate corresponding pails throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION

As schematically illustrated in FIG. 1, injection device 20 includes a housing 22 and is used with a medicament cartridge 24. Cartridge 24 is a conventional medicament cartridge having a pierceable septum secured with a crimped seal 27, a piston 30 and storing a medicament 28. Housing 22 includes a cartridge holder 32 in which cartridge 24 is installed. A needle assembly 26 is attachable to the distal end of cartridge holder 32. After installing cartridge 24 in cartridge holder 32, needle assembly 26 is secured to cartridge holder 32. Attachment of needle assembly 26 pierces the septum of assembly 27 to allow the medicament to be expelled through the needle assembly 26. After inserting the needle of assembly 26 in a patient, piston 30 is advanced forcing medicament 28 out of needle assembly 26 and into the patient.

Housing 22 at least partially encloses the various parts of injection device 20 and provides a convenient structure for the user to grasp when employing device 20. Housing 22 includes both cartridge holder 32 and a main housing 34 which contains the drive assembly 36. Detaching cartridge holder 32 from main housing 34 allows a depleted cartridge 24 to be removed and replaced with a fresh cartridge 24.

Drive assembly 36 includes an actuator assembly 38, a drive member 40, a first gearing arrangement 42 and a second gearing arrangement 44. The first gearing arrangement 42 couples drive member 40 with plunger 46 which, in turn, is engaged with piston 30 to couple plunger 46 with cartridge 24. Advancement of plunger 46 when coupled with cartridge 24 expels medicament from cartridge 24. Second gearing arrangement 44 couples drive member 40 with dosage indicator 48 to thereby provide feedback to the user indicating the set dosage.

Drive member 40 has an elongate shaft 52 and defines an axis 50. Drive member 40 is both rotatable about axis 50 and translatable in a first axial direction 58 and an opposite second axial direction 60. Drive member 40 also defines a first gear pattern 54 which is a part of the first gearing arrangement 42 and a second gear pattern 56 which is part of the second gearing arrangement 44. As can be seen in FIG. 1, first and second gear patterns 54, 56 are axially displaced relative to each other and fixed relative to each other on common shaft 52.

In the illustrated embodiment first gear pattern 54 is a worm gear having a single thread 62 while the second gear pattern 56 is formed by a plurality of annular gear teeth 64 defining a pitch angle of 0 degrees. As will become evident from the discussion which follows below, this allows the rotation of drive member 40 to drive the first gearing arrangement 42 without driving the second gearing arrangement 44 when such rotation is not accompanied by axial translation of drive member 40.

First gearing arrangement 42 operably couples the first gear pattern 54 with the plunger 46 such that rotation of drive member 40 in a first rotational direction 78 translates drive member 40 in the first axial direction 58 without movement of the plunger 46 and translation of the drive member 40 in the second axial direction 60 drives the plunger 46 in the advancing direction 70.

When the user desires to set a dosage amount, the user will rotate actuator assembly 38 in rotational direction 78 (FIG. 1) which, in turn, will cause rotation of drive member 40 in rotational direction 78. First gear pattern 54 is engaged with a first rotatable gear member 80 and when drive member 40 is rotated in direction 78, a one-way clutch 82 prevents gear member 80 from rotating in the direction it is being urged by drive member 40. As a result of gear member 80 remaining stationary, drive member 40 will be axially retracted in direction 58 as it is rotated in direction 78. This axial retraction of drive member 40 sets the dosage. Because gear member 80 is stationary, plunger 46 will also remain stationary when the dosage is being set and the inadvertent discharge of medicament due to forward motion of plunger 46 will thereby be inhibited.

Figure 2:
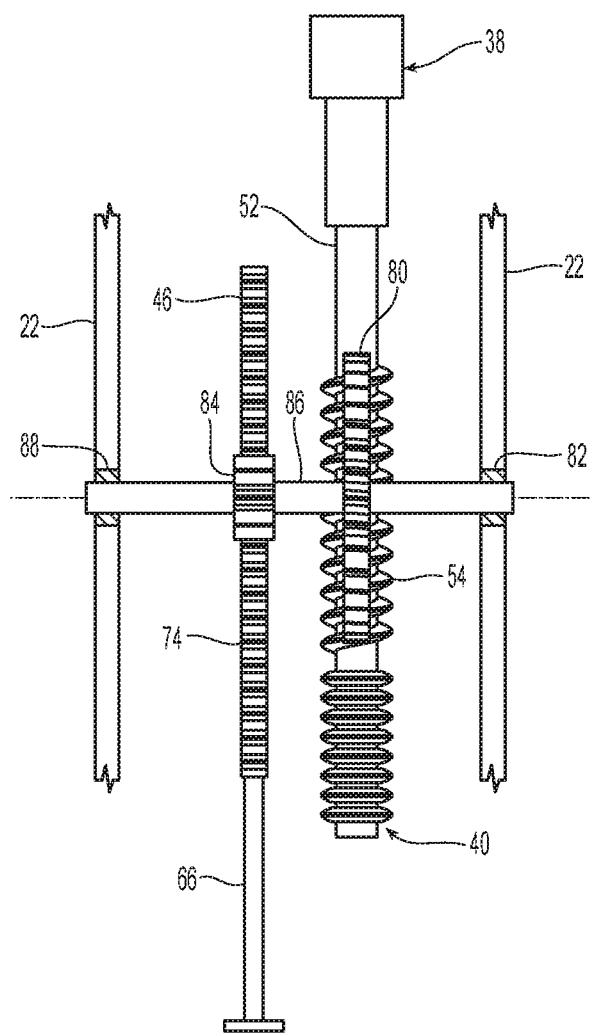
FIG. 2 is a schematic representation of a drive member and a first gearing arrangement.

FIG. 2 schematically depicts gear 80 which is mounted on shaft 86. One-way clutch 82 prevents rotation of shaft 86 when the drive member 40 is rotated in the first rotational direction 78. One-way clutch 82 may take the form of a ratchet and pawl arrangement or other suitable mechanism for providing a one-way clutch which are well-known to those having ordinary skill in the art. Bearing 88 which supports the end of shaft 86 opposite one-way clutch 82 may be either a simple bearing or a one-way clutch which blocks rotation of shaft 86 in the same direction as one-way clutch 82.

After setting, the dose, the user will depress actuator assembly 38 causing the axial advancement of drive member 40 in the second axial direction 60 to thereby drive plunger 46 in an advancing direction 70. The advancing direction 70 and retraction direction 72 of plunger 46 are indicated with arrows in FIG. 1. Plunger 46 is coupled with cartridge 24 by engaging plunger head 68 with piston 30 whereby medicament 28 is expelled from cartridge 24 when plunger 46 is translated in the advancing direction 70. As discussed below, when the user depresses actuator assembly 38 to axially translate drive member 40 in axial direction 60, drive member 40 is prevented from rotating about its axis 50 to thereby ensure that axial advancement of drive member 40 results in the rotation of gear member 80.

As can be seen in FIG. 1, plunger 46 has an elongate stem 66 with plunger head 68 being disposed at its distal end for engagement with piston 30. A rack 74 is disposed on stem 66 such that axial translation of rack 74 causes a similar axial translation of plunger 46. In some embodiments, rack 74 could be directly engaged with gear member 80. In the illustrated embodiment, however, a second rotatable gear member 84 is coupled with first gear member 80 and rack 74. More specifically, in the illustrated embodiment, gear member 84 is engaged with rack 74 and both gear members 80, 84 are fixed to the same shaft 86. As a result, when gear member 80 rotates, this rotation is transmitted through shaft 86 to gear member 84 which is engaged with rack 74.

In the illustrated embodiment, gear members 80, 84 define a non-unitary gear ratio. In the illustrated embodiment the gear ratio is approximately 3:1. The use of a non-unitary gear ratio allows the gear members 80, 84 to define a reduction gear to thereby facilitate user-friendly operation of device 20. In operation, when drive member 40 is axially advanced in direction 60 without rotation of drive member 40, this causes gear member 80 to rotate. This, in turn rotates gear member 84 which thereby causes rack 74 and plunger 46 to be axially translated in advancing direction 70.

Second gearing arrangement 44 is coupled with dosage indicator 48 and facilitates the correct setting of desired dosage. It is noted that second gearing arrangement 44 and dosage indicator 48 have been omitted from FIGS. 1 and 2 for purposes of graphical clarity. The operation of second gearing arrangement 44 and dosage indicator 48 is best understood with reference to FIGS. 3 and 4. It will be understood that first gearing arrangement 42 has been omitted from FIGS. 3 and 4 for purposes of graphical clarity.

Second gearing arrangement 44 operably couples the second gear pattern 56 with the dosage indicator 48. Second gearing arrangement 44 moves the dosage indicator 48 to indicate an increase in the set dosage when the drive member 40 is translated in the first axial direction 58.

Figure 5:
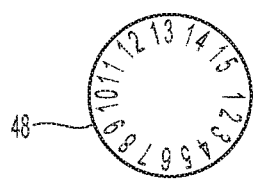
FIG. 5 is a view of a dosage indicator.
Figure 6:
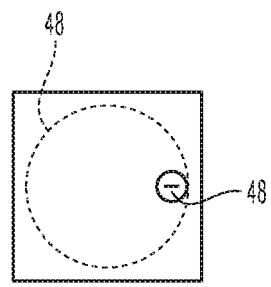
FIG. 6 is another view of the dosage indicator.

Movement of dosage indicator 48 provides a visible indicator to the user which lets the user know the dosage which has been set. FIG. 5 illustrates one embodiment of a dosage indicator 48 which includes a dial having a series of numbers printed or embossed proximate its outer circumference. As dosage indicator 48 rotates, the numbers are sequentially rotated past a pointer or window to indicate which one of the numbers accurately reflects the dosage which has been set. FIG. 6 illustrates one example of how dosage indicator 48 may be positioned behind a cover plate or a portion of housing 22 with a window allowing the number on indicator 48 which accurately reflects the set dosage to be seen through a window or cutout.

Figure 3:
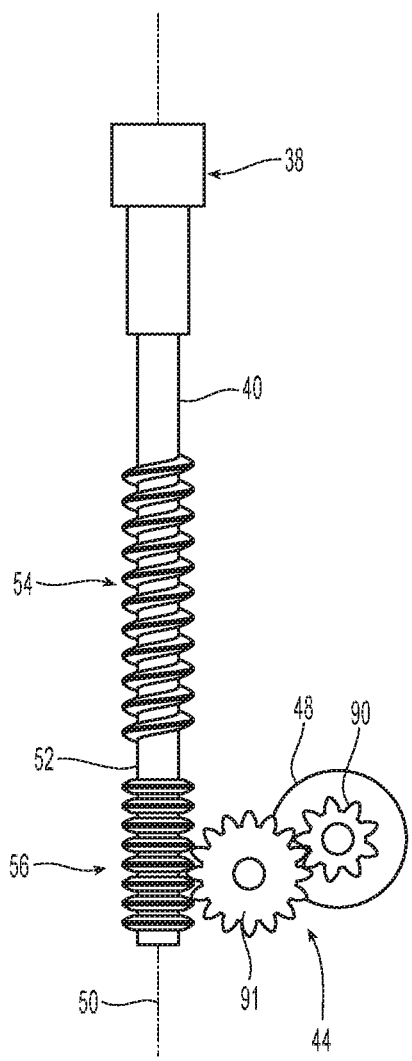
FIG. 3 is a schematic representation of a drive member and a second gearing arrangement.
Figure 4:
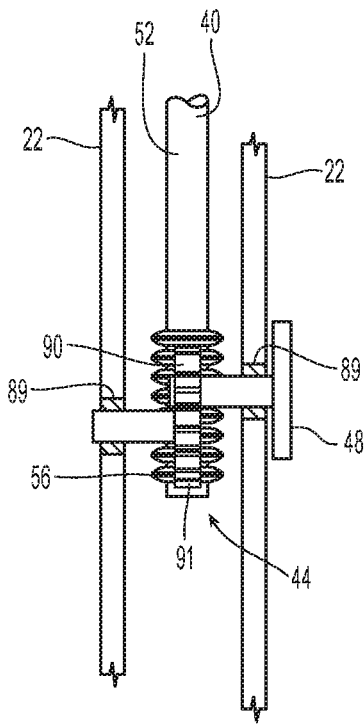
FIG. 4 is another schematic representation of the second gearing arrangement.

As best understood with reference to FIGS. 3 and 4, second gearing arrangement 44 rotates dosage indicator 48 as drive member 40 is retracted in direction 58. Because second gear pattern 56 is formed by annular gear teeth having a pitch angle of 0 degrees, movement of the second gearing arrangement 44 generated by the drive member 40 is exclusively due to the axial translation of the drive member 40 and movement of the second gearing arrangement 44 is independent of the rotational position and rotational movement of the drive member 40.

Second gearing arrangement 44 includes a third rotatable gear member 91 that is engaged with the second gear pattern 56 and is operably coupled with the dosage indicator 48. In the illustrated embodiment, gear member 91 is operably coupled with dosage indicator 48 via engagement with fourth rotatable gear member 90. Dosage indicator 48 is fixed relative to fourth gear member 90. In alternative embodiments, a single gear member could be used instead of gear members 90, 91. Suitable bearing arrangements 89 provide rotatable support for gear members 90, 91. The ratio of gear members 90, 91 is selected so that it provides an appropriate dose indication based on the axial displacement of drive member 40.

In the illustrated embodiment, axial translation of drive member 40 rotates gear members 90, 91 and dosage indicator 48 in both axial directions 58, 60. As a result, when drive member 40 is translated in first axial direction 58, second gearing arrangement 44 causes dosage indicator 48 to rotate in a manner that indicates an increasing dosage as drive member 40 continues to translate in direction 58. As discussed above, rotation of drive member 40 in direction 78 causes drive member 40 to be axially translated in direction 58 when setting a dosage. When drive member 40 is axially translated in direction 60 by depression of actuator assembly 38, second gearing arrangement 44 will move the dosage indicator 48 to indicate a decrease in the set dosage. Once drive member 40 has been fully advanced in axially direction 60, dosage indicator 48 will return to its initial position. This configuration allows the user to see from the position of dosage indicator 48 how much of the set dosage must still be injected to inject the entire set dosage. The user will also be able to see from the return of dosage indicator 48 to its original position when the entire set dosage has been expelled from cartridge 24.

In alternative embodiments of second gearing arrangement 44, a one-way clutch could be integrated into gearing arrangement 44 such that dosage indicator 48 does not move as drive member 40 is advanced in axial direction 60. In such an embodiment (not shown), it may be advantageous to include a mechanism which provides an audible click or tactile feedback to the user when drive member 40 is fully advanced in axial direction 60 to complete an injection. In such an embodiment, it may also be advantageous for the dosage indicator to be capable of being reset to its zero position after an injection. For example, a cover plate having a window through which a single digit of dosage indicator 48 is viewable might be rotatable about the same axis as dosage indicator 48 whereby the cover plate is repositioned to expose the zero position of the dosage indicator 48 after completing an injection.

The user sets the dosage and delivers the medicament by manipulating actuator assembly 38. As discussed above, the user rotates actuator assembly 38 in rotational direction 78 to retract drive member 40 in axial direction 58 to set the dosage. Depression of actuator assembly in direction 60 advances drive member in axial direction 60 to deliver the medicament.

Figure 7:
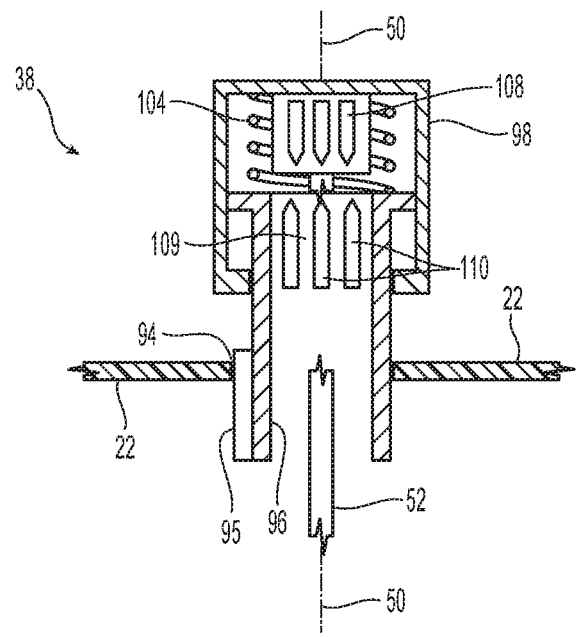
FIG. 7 is a schematic representation of the actuator assembly.
Figure 8:
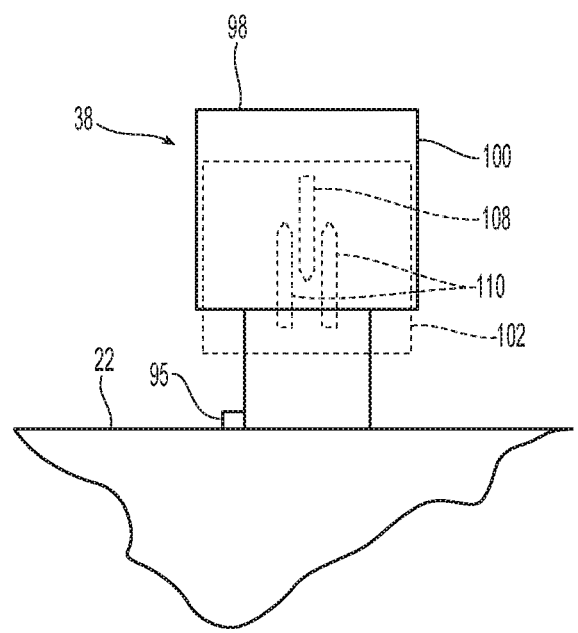
FIG. 8 is another schematic representation of the actuator assembly.

The operation of actuator assembly 38 is best understood with reference to FIGS. 7 and 8. Actuator assembly 38 is operably coupled with drive member 40 and, in the illustrated embodiment, shaft 52 of drive member 40 is fixed to actuating member 98. The illustrated embodiment of actuating assembly 38 also includes a sleeve member 96 which is axially slidable relative to housing 22. Sleeve member 96 has a projection 95 or similar feature that slides within a slot 94 on housing 22 and thereby prevents rotation of sleeve 96 about axis 50. Sleeve 96 is generally tubular in shape. Shaft 52 extends through the center of sleeve 96 with sleeve 96 and shaft 52 being disposed substantially concentrically about axis 50.

The interior surface of sleeve 96 is generally cylindrical and defines a plurality of axially extending splines 110. Not all of the splines 110 are illustrated in FIGS. 7 and 8 for purposes of graphical clarity. Splines 110 are extend around the full circumference of sleeve 96 and are equally spaced. Splines 110 define keyways 109 between adjacent splines 110. Because projection 95 prevents sleeve 96 from rotating about axis 50, keyways 109 are also rotationally fixed relative to axis 50.

Actuating member 98 is axially moveable relative to sleeve 96 and keyways 109 disposed thereon between a dose setting position 100 and an injection position 102 as schematically depicted in FIG. 8. Actuating member 98 includes a plurality of splines 108 which are slidable into keyways 109 defined by splines 110. In the dose setting position 100, splines 108 are spaced axially from splines 110 and keyways 109 thereby allowing actuating member 98 to be rotated about axis 50 in direction 78. Rotation of actuating member 98 in direction 78 will rotate drive member 40 in direction 78 to thereby set a dosage. FIG. 7 depicts actuating member 98 in dose setting position 100.

A biasing member 104 is operably coupled with the actuating member 98 and biases actuating member 98 toward the dose setting position 100. In the illustrated embodiment, biasing member 104 is a coil spring positioned between sleeve 96 and actuating member 98. As can be seen in FIG. 7, flanges on actuating member 98 and sleeve 96 capture actuating member 98 on sleeve 96 and limit the axial distance actuating member 98 can be biased away from sleeve 96. As mentioned above, actuating member 98 is attached to shaft 52 which thereby captures actuating member 98 and sleeve 96 on device 20.

When the user begins an injection, the user depresses actuating member 98 forcing it in axial direction 60. As actuating member 98 is advanced, spring 104 is compressed and splines 108 slide into keyways 109 between splines 110 and thereby placing actuating member 98 in its injection position 102. When actuating member 98 is in this injection position 102, the engagement of splines 108 with keyways 109 rotationally fixes actuating member 98 relative to axis 50.

Because actuating member 98 is both rotationally and axially coupled with drive member 40, as actuating member 98 is further advanced in axial direction 60, drive member 40 is also axially advanced in direction 60 and is unable to rotate because splines 108 and 110 prevent the rotation of actuating member 98. This axial advancement of drive member 40 without rotation causes the rotation of gear 80 and thereby causes first gearing arrangement 42 to advance plunger 46 in direction 70.

In the illustrated embodiment, sleeve member 96 and actuating member 98 are axially aligned with drive member 40 with the sleeve member 96 being non-rotationally slidable relative to housing 22 in the first and second axial directions 58, 60 and with biasing member 104 being operably disposed between sleeve member 96 and actuating member 98. Alternative embodiments, however, may also be used. For example, it is not necessary to employ a sleeve 96. Instead, a keyway could be disposed on housing 22 to engage a feature on actuating member 98 to prevent its rotation when it is in an injection position. The use of sleeve 96 can be advantageous, however, because it facilitates lengthened axial travel distances.

It is further noted that while the embodiment of FIG. 7 shows that shaft 52 has an enlarged diameter portion on which splines 108 are disposed, other embodiments might have a shaft 52 which does not require an enlarged diameter portion. Moreover, various other mechanisms could be employed to provide for the same control over the axial and rotational movement of actuating member 98 that is achieved with actuating assembly 38.

After one or more injections has depleted cartridge 24, the cartridge is removed and replaced with a fresh cartridge. Before installing a new cartridge 24, plunger 46 is retracted in axial direction 72. To provide for the retraction of plunger 46, plunger stem 66 may include laterally extending pins (not shown) that ride in slots (not shown) in housing 22. When plunger 46 has reached to limit of its axial travel in advancing direction 70, the slots could be configured to displace stem 66 relative to gear 84 and thereby disengage rack 74 from gear 84 enabling plunger 46 to be retracted. Various other mechanisms could also be employed to provide for the retraction of plunger 46. For example, one-way gear 82 could be disengaged to allow for the retraction of plunger 46 in direction 72 while rack 74 is still engaged with first gearing arrangement 42. For example, on a pawl and ratchet one-way clutch a lever on the pawl could be used to disengage the pawl and permit retraction of plunger 46. Those having ordinary skill in the art will recognize that various other arrangement may also be used to provide for the retraction of plunger 46 before installing a new cartridge 24.

While this invention has been described as having an exemplary design, the present invention may be further modified within the spirit and scope of this disclosure. This application is therefore intended to cover any variations, uses, or adaptations of the invention using its general principles.

What is claimed is:

1. An injection device for use with a medicament cartridge, the injection device comprising:
    a drive member having an elongate shaft and defining an axis and having first and second gear patterns, wherein the first and second gear patterns are fixed relative to each other and formed along an exterior of the shaft that is common for the first and second gear patterns, the drive member being rotatable about the axis and translatable in first and second opposing axial directions;
    a plunger having an elongate stem, the plunger being couplable with the cartridge to expel medicament from the cartridge when the plunger is translated in an advancing direction;
    a dosage indicator, the dosage indicator being moveable to indicate a set dosage;
    a first gearing arrangement operably coupling the first gear pattern with the plunger wherein in response to a rotation of the drive member in a first rotational direction the drive member is translated in the first axial direction without movement of the plunger, and wherein in response to a translation of the drive member in the second axial direction the plunger is driven in the advancing direction; and
    a second gearing arrangement operably coupling the second gear pattern with the dosage indicator, wherein in response to the drive member being translated in the first axial direction the second gearing arrangement is configured to move the dosage indicator to indicate an increase in the set dosage.

2. The injection device of claim 1 wherein the first and second gear patterns are axially displaced relative to each other.

3. The injection device of claim 2 wherein the first gearing arrangement comprises a first rotatable gear member engaged with the first gear pattern and a one-way clutch operably coupled with the first rotatable gear member, wherein the one-way clutch is configured to prevent rotation of the first gear member when the drive member is rotated in the first rotational direction and wherein in response to the translation of the drive member in the second axial direction the first gear member is rotated to thereby drive the plunger.

4. The injection device of claim 3 wherein the first gearing arrangement further comprises a second rotatable gear member coupled with the first rotatable gear member and a rack coupled with the plunger, the second rotatable gear member being engageable with the rack.

5. The injection device of claim 4 wherein the first and second rotatable gear members define a non-unitary gear ratio, wherein the drive member comprises a single piece shaft and the first and second gear patterns are axially displaced relative to each other along the single piece shaft.

6. The injection device of claim 5 wherein the first and second rotatable gear members are fixed to a common shaft.

7. The injection device of claim 6 wherein the first gear pattern defines a worm gear.

8. The injection device of claim 5 wherein a movement of the second gearing arrangement generated by the drive member is exclusively due to the translation of the drive member and movement of the second gearing arrangement is independent of the rotation of the drive member.

9. The injection device of claim 5 wherein the second gearing arrangement is configured to move the dosage indicator to indicate a decrease in the set dosage when the drive member is translated in the second axial direction.

10. The injection device of claim 5 wherein the second gearing arrangement comprises a third rotatable gear member engaged with the second gear pattern and operably coupled with the dosage indicator.

11. The injection device of claim 10 wherein the dosage indicator is fixed relative to the third rotatable gear member.

12. The injection device of claim 11 wherein the second gear pattern comprises a plurality of annular gear teeth defining a pitch angle of 0 degrees.

13. The injection device of claim 12 further comprising:
a housing at least partially enclosing the injection device; and
a manually operable actuator assembly operably coupled with the drive member, the actuator assembly being at least partially disposed external to the housing wherein the actuator assembly includes an actuating member that is rotatable to set a selected dose and axially translatable to inject the selected dose.

14. The injection device of claim 13 wherein the actuator assembly further comprises:
a keyway disposed proximate the drive member and rotationally fixed relative to the drive member axis;
the actuating member being axially moveable relative to the keyway between a dose setting position and an injection position, the actuating member being rotationally and axially coupled with the drive member wherein, in the dose setting position the actuating member is rotatable about the drive member axis and rotation of the actuating member rotates the drive member and, in the injection position, the actuating member is engaged with the keyway thereby rotationally fixing the actuating member relative to the drive member axis and wherein axial movement of the actuating member in the second axial direction drives the drive member in the second axial direction;
a biasing member operably coupled with the actuating member and biasing the actuating member toward the dose setting position.

15. The injection device of claim 14 further comprising a sleeve member, the sleeve member being rotationally fixed relative to the drive member axis and having the keyway disposed thereon.

16. The injection device of claim 15 wherein the sleeve member and the actuating member are axially aligned with the drive member, wherein the sleeve member is non-rotationally slidable relative to the housing in the first and second axial directions and wherein the biasing member is operably disposed between the sleeve member and the actuating member.

17. An injection device for use with a medicament cartridge having a needle end to receive a needle assembly, the injection device comprising:
a drive member defining an axis and having first and second gear patterns, wherein the first and second gear patterns are fixed relative to each other and formed along an exterior of a common shaft, wherein the first gear pattern comprises a worm gear, the second gear pattern comprises a plurality of annular gear teeth defining a pitch angle of 0 degrees axially displaced relative to the worm gear toward a needle end, the drive member being rotatable about the axis and translatable in first and second opposing axial directions;
a plunger having an elongate stem, the plunger being couplable with the cartridge to expel medicament from the cartridge when the plunger is translated in an advancing direction;
a dosage indicator, the dosage indicator being moveable to indicate a set dosage;
a first gearing arrangement operably coupling the first gear pattern with the plunger, wherein in response to a rotation of the drive member in a first rotational direction the drive member is translated in the first axial direction without movement of the plunger, and wherein in response to a translation of the first gear pattern of the drive member in the second axial direction relative to the first gearing arrangement the plunger is driven in the advancing direction; and
a second gearing arrangement operably coupling the second gear pattern with the dosage indicator, wherein in response to the drive member being translated in the first axial direction the second gearing arrangement is configured to move the dosage indicator to indicate an increase in the set dosage.

18. The injection device of claim 17, and wherein a movement of the second gearing arrangement generated by the drive member is exclusively due to the translation of the drive member and said movement of the second gearing arrangement is independent of the rotation of the drive member.

19. An injection device for use with a medicament cartridge, the injection device comprising:
a drive member having an elongate shaft and defining an axis and having first and second gear patterns of annular members formed along an exterior of the shaft of the drive member, wherein the first and second gear patterns are fixed relative to each other, the drive member being rotatable about the axis and translatable in first and second opposing axial directions;
a plunger having an elongate stem, the plunger being couplable with the cartridge to expel medicament from the cartridge when the plunger is translated in an advancing direction;
a dosage indicator, the dosage indicator being moveable to indicate a set dosage;
a first gearing arrangement operably coupling the first gear pattern with the plunger, wherein in response to a rotation of the drive member in a first rotational direction the drive member is translated in the first axial direction without movement of the plunger, and wherein in response to translation of the drive member in the second axial direction the plunger is driven in the advancing direction; and
a second gearing arrangement operably coupling the second gear pattern with the dosage indicator, wherein in response to the drive member being translated in the first axial direction the second gearing arrangement is configured to move the dosage indicator to indicate an increase in the set dosage.

20. The injection device of claim 19, wherein the first gearing arrangement comprises a first rotatable gear member engaged with the first gear pattern and a one-way clutch operably coupled with the first rotatable gear member, wherein the one-way clutch is configured to prevent rotation of the first gear member when the drive member is rotated in the first rotational direction, and wherein in response to translation of the drive member in the second axial direction the first gear member is rotated to thereby drive the plunger, and wherein a movement of the second gearing arrangement generated by the drive member is exclusively due to the translation of the drive member and said movement of the second gearing arrangement is independent of the rotation of the drive member.

\* \* \* \* \*